(12) United States Patent
Gruba et al.

(10) Patent No.: US 12,016,879 B2
(45) Date of Patent: Jun. 25, 2024

(54) CALCIUM ELECTROPORATION DELIVERY APPARATUS AND METHOD

(71) Applicants: Boston Scientific Scimed, Inc., Maple Grove, MN (US); Mayo Foundation for Medical Education and Research, Rochester, MN (US)

(72) Inventors: Sarah M. Gruba, Vadnais Heights, MN (US); Douglas D. Pagoria, Forest Lake, MN (US); James P. Rohl, Prescott, WI (US); Stephen J. Hahn, Shoreview, MN (US); Suraj Kapa, Rochester, MN (US); Chance M. Witt, Rochester, MN (US)

(73) Assignees: Boston Scientific Seimed, Inc., Maple Grove, MN (US); Mayo Foundation For Medical Education And Research, Rochester, MN (US)

( * ) Notice: Subject to any disclaimer, the term of this patent is extended or adjusted under 35 U.S.C. 154(b) by 1188 days.

(21) Appl. No.: 16/171,678

(22) Filed: Oct. 26, 2018

(65) Prior Publication Data
US 2019/0125788 A1    May 2, 2019

Related U.S. Application Data

(60) Provisional application No. 62/577,824, filed on Oct. 27, 2017.

(51) Int. Cl.
*A61B 18/14* (2006.01)
*A61K 9/00* (2006.01)
(Continued)

(52) U.S. Cl.
CPC .......... *A61K 33/06* (2013.01); *A61B 18/1492* (2013.01); *A61K 9/0009* (2013.01);
(Continued)

(58) Field of Classification Search
CPC ...... A61K 33/06; A61K 9/0009; A61K 33/14; A61K 33/42; A61K 9/0004; A61K 9/0024;
(Continued)

(56) References Cited

U.S. PATENT DOCUMENTS 6,629,947 B1 * 10/2003 Sahatjian ......... A61B 17/12022
                                                                        604/11
6,758,847 B2 *  7/2004 Maguire ................... A61N 7/02
                                                                        606/41
(Continued)

FOREIGN PATENT DOCUMENTS

WO    2017062753 A1    4/2017
WO    WO-2017062753 A1 *   4/2017    ......... A61B 1/00082

OTHER PUBLICATIONS

Frandsen, S.K., et al., "Calcium Electroporation: Evidence for Differential Effects in Normal and Malignant Cell Lines, Evaluated in a 3D Spheroid Model", PLoS ONE 10(12): e0144028 (2015), 11 pages.
(Continued)

*Primary Examiner* — Thomas A Giuliani
(74) *Attorney, Agent, or Firm* — Seager, Tufte & Wickhem, LLP

(57) ABSTRACT

In various aspects, the present disclosure provides methods for applying ablation therapy to a target tissue region within a patient, which methods include: (a) navigating a catheter to a target tissue region within the patient, the catheter including an elongate body having a proximal portion and a distal portion and a balloon structure positioned at the distal portion of the elongate body, which balloon structure may be permeable to a calcium-ion-containing solution that comprises one or more calcium salts; (b) positioning the balloon structure at the target tissue region; (c) delivering energy to the target tissue region; and (d) eluting the calcium-ion-
(Continued)

containing solution from the balloon structure before, during, and/or after delivering the energy to the target tissue region. In various other aspects, the present disclosure provides apparatuses that can be used for performing such methods, among others.

7 Claims, 5 Drawing Sheets

(51) Int. Cl.
*A61K 33/06* (2006.01)
*A61K 33/14* (2006.01)
*A61K 33/42* (2006.01)
*A61B 18/00* (2006.01)

(52) U.S. Cl.
CPC ............. *A61K 33/14* (2013.01); *A61K 33/42* (2013.01); *A61B 2018/0022* (2013.01); *A61B 2018/00238* (2013.01); *A61B 2018/00351* (2013.01); *A61B 2018/00577* (2013.01); *A61B 2018/00613* (2013.01); *A61B 2018/00839* (2013.01)

(58) Field of Classification Search
CPC .............. A61K 9/0092; A61K 9/025; A61K 2039/505; A61K 33/08; A61K 33/10; A61K 33/12; A61B 18/14; A61B 18/1492; A61B 2018/0022; A61B 2018/00238; A61B 2018/00351; A61B 2018/00577; A61B 2018/00613; A61B 2018/00839; A61B 2018/00255; A61B 2018/00345; A61B 2018/00583; A61B 2018/00214; A61B 2018/00232; A61B 18/0218; A61B 2018/0212; A61B 2018/00482; A61B 2018/00505; A61B 2018/1465; A61B 2218/002; A61B 2218/001; A61B 2018/00273; A61B 2018/00279; A61B 2018/00285; A61B 2018/00065; A61B 2018/1472; C07K 2317/76; C07K 2317/73; A61P 43/00; A61P 9/00
USPC ...... 606/32–34, 40–42, 49; 607/98, 99, 104, 607/113, 115, 116
See application file for complete search history.

(56) References Cited

U.S. PATENT DOCUMENTS

| | | | | |
|---|---|---|---|---|
| 2002/0183684 | A1* | 12/2002 | Dev | A61N 1/325 977/932 |
| 2002/0188289 | A1* | 12/2002 | Hegde | A61B 18/1492 606/41 |
| 2003/0212394 | A1* | 11/2003 | Pearson | A61B 18/1477 606/41 |
| 2004/0106841 | A1 | 6/2004 | Shaw et al. | |
| 2007/0032787 | A1* | 2/2007 | Hassett | A61B 18/1492 606/41 |
| 2010/0125239 | A1* | 5/2010 | Perry | A61L 29/08 604/509 |
| 2013/0261368 | A1 | 10/2013 | Schwartz | |
| 2014/0163601 | A1* | 6/2014 | Stamberg | A61L 29/14 425/174.8 E |
| 2014/0163664 | A1 | 6/2014 | Goldsmith | |
| 2017/0266419 | A1* | 9/2017 | Goshayeshgar | A61M 39/02 |

OTHER PUBLICATIONS

Mattson, M.P., and Chan, S.L., "Calcium orchestrates apoptosis", Nature Cell Biology 5(12):1041-1043 (2003).
Nicotera, P., and Orrenius, S., "The role of calcium in apoptosis", Cell Calcium 23(2/3):173-180 (1998).
International Search Report and Written Opinion for application No. PCT/US2018/057680, dated Jan. 24, 2019, 9 pages.

* cited by examiner

CALCIUM ELECTROPORATION DELIVERY APPARATUS AND METHOD

CROSS REFERENCE TO RELATED APPLICATIONS

This application claims the benefit of priority under 35 U.S.C. § 119 to U.S. Provisional Patent Application Ser. No. 62/577,824, filed on Oct. 27, 2017, which is incorporated by reference in its entirety for all purposes.

BACKGROUND

Atrial fibrillation is an irregular and often rapid heart rate that commonly causes poor blood flow to the body. Ablation procedures, including ablation of thoracic veins such as the pulmonary veins, have been proposed as a treatment for atrial fibrillation. During pulmonary vein ablation, for example, catheters are inserted into the atrium and energy is delivered to the tissue of a pulmonary vein and/or near the ostia of the pulmonary vein in the left atrium. During such procedures, a health care professional may unintentionally under-ablate a desired treatment area causing only reversible electroporation an area where irreversible electroporation is desired or may wish to expand the zone of cell death to peripheral areas where only reversible electroporation would otherwise occur.

SUMMARY

In various aspects, the present disclosure provides methods for applying ablation therapy to a target tissue region within a patient, which methods include: (a) navigating a catheter to a target tissue region within the patient, the catheter including an elongate body having a proximal portion and a distal portion and a balloon structure positioned at the distal portion of the elongate body, which balloon structure may be permeable to a calcium-ion-containing solution that comprises one or more calcium salts; (b) positioning the balloon structure at the target tissue region; (c) delivering energy to the target tissue region; and (d) eluting the calcium-ion-containing solution from the balloon structure before, during, and/or after delivering the energy to the target tissue region.

In various embodiments, which may be used in conjunction with the above aspects, the calcium-ion-containing solution may comprise one or more calcium salts selected from calcium halide salts, calcium salts of organic acids, calcium phosphate, and combinations thereof. In certain embodiments, the calcium-ion-containing solution may comprise calcium chloride.

In various embodiments, which may be used in conjunction with the above aspects and embodiments, a concentration of calcium ions in the calcium-ion-containing solution may be at least 250 nanomolar (nM). In certain embodiments, which may be used in conjunction with the above aspects and embodiments, a concentration of calcium ions in the calcium-ion-containing solution may range from 250 nM to 500 millimolar (mM).

In various embodiments, which may be used in conjunction of the above aspects and embodiments, a solution containing a Group 1A metal halide salt may be eluted from the balloon structure before and/or during delivery of the energy to the target tissue region, and the calcium-ion-containing solution may be eluted after delivery of the energy to the target tissue region.

In various aspects, which may be used in conjunction of the above aspects and embodiments, the present disclosure provides an apparatus comprising: (a) an electroporation catheter that comprises (i) a balloon structure, which comprises an interior chamber and is permeable to a calcium-ion-containing solution that comprises one or more calcium salts, and (ii) an elongate body having a proximal end and a distal end, which balloon structure is positioned at the distal end of the elongate body; and (b) one or more first containers containing (i) the calcium-ion-containing solution or (ii) the one or more calcium salts in dry form, which produces the calcium-ion-containing solution upon mixing with a liquid carrier.

In various embodiments, which may be used in conjunction with the above aspects and embodiments, the one or more first containers may be selected from a syringe, and a vial having a rubber septum.

In various embodiments, which may be used in conjunction with the above aspects and embodiments, a concentration of calcium ions in the calcium-ion-containing solution may be at least 250 nM, commonly ranging from 250 nM to 500 mM.

In various embodiments, which may be used in conjunction with the above aspects and embodiments, the one or more calcium salts of the calcium-ion-containing solution may be selected from calcium halide salts, calcium salts of organic acids, calcium phosphate and combinations thereof.

In various embodiments, which may be used in conjunction with the above aspects and embodiments, apparatus may comprise (a) the one or more first containers containing the one or more calcium salts in dry form and (b) one or more second containers containing the liquid carrier.

In various embodiments, which may be used in conjunction with the above aspects and embodiments, (a) the catheter is configured to be navigated to a target tissue region within patient such that the balloon is positioned at a target tissue region, (b) the catheter is configured to deliver energy to the target tissue region; and (c) the catheter is configured to elute the calcium-ion-containing solution from the balloon structure.

In various embodiments, which may be used in conjunction with the above aspects and embodiments, the balloon structure of the catheter may comprise a first region that is permeable to the calcium-ion-containing solution and a second region that is substantially impermeable to the calcium-ion-containing solution. For example, the first region of the balloon structure may be a porous region (e.g., a porous band, porous strip, etc.) and the second region of the balloon structure may be a non-porous region.

In various embodiments, which may be used in conjunction with the above aspects and embodiments, the balloon structure of the catheter may comprise an electrospun balloon.

In various embodiments, which may be used in conjunction with the above aspects and embodiments, the elongate body of the catheter may comprise a lumen in fluid communication with the interior chamber, which lumen is configured to supply the calcium-ion-containing solution to the interior chamber such that the calcium-ion-containing solution permeates through the first region of the balloon structure.

In various embodiments, which may be used in conjunction with the above aspects and embodiments, an electrode may be positioned within the interior chamber of the balloon structure.

In various embodiments, which may be used in conjunction with the above aspects and embodiments, the apparatus may further comprise a controller configured to supply electrical energy to the catheter.

Additional details of various aspects and embodiments of the disclosure are set forth in the description to follow and in the accompanying drawings. Other features and advantages of the present disclosure will be apparent from the description, drawings, and claims provided hereinbelow.

DETAILED DESCRIPTION

Figure 1:
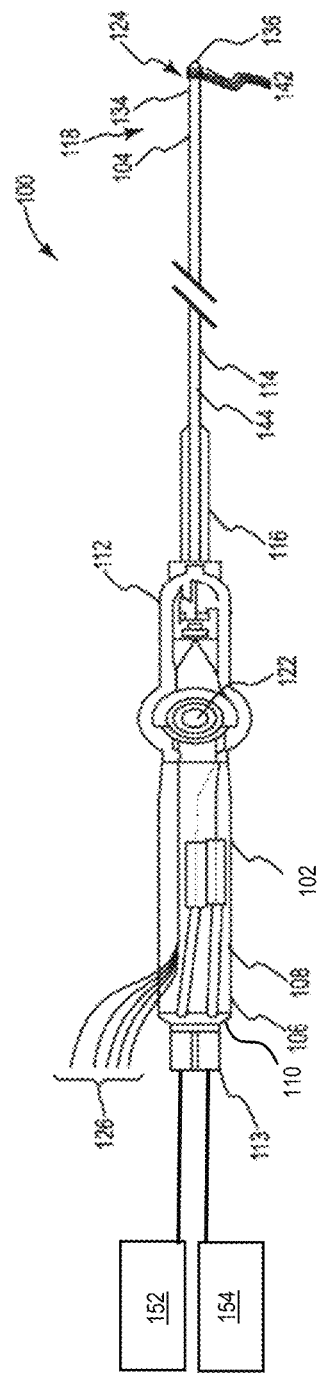
FIG. 1 shows an exemplary ablation system in accordance with embodiments of the disclosure.

To prevent abnormal electrical signals in the heart that cause arrhythmias (e.g., atrial fibrillation, post-infarction re-entrant cycles in areas that are a mix of scar and healthy myocardium, etc.), health care professionals will frequently ablate heart tissue using a variety of techniques. A health care professional may also wish to ablate a portion of the heart (e.g., the left atrial appendage) to reduce the likelihood of an implanted medical device being dislodged. One way to ablate these cells is to use irreversible electroporation, which causes the formation of pores in the cells and then cell death. In this regard, the electric field is believed to cause apoptosis and/or non-thermal necrosis of the cells receiving electrical energy.

If a health care professional does not use enough power to properly ablate cells or wants to extend the ablation zone to cells that are merely undergoing reversible electroporation at the edge of the electric field, additional methods of cell destruction that will not damage nearby tissue would be desirable. Using the pores that are formed during reversible and irreversible electroporation provides the potential to infuse chemical species, including calcium ions, into the cells.

To help promote additional cell death associated with irreversible electroporation treatment of target tissue, in accordance with one aspect of the present disclosure, calcium ions ($Ca^{2+}$) are delivered to the target tissue before, during, and/or after the electroporation treatment is administered.

A potential benefit of delivering calcium ions is that areas of irreversible electroporation may be created in areas where only reversible electroporation would otherwise occur in the absence of the calcium ions, thereby increasing the effectiveness of the irreversible electroporation treatment. For example, during an electroporation procedure, a health care professional (a) may unintentionally under-ablate a targeted treatment area causing only reversible electroporation, (b) may wish to expand a zone of cell death to peripheral areas where only reversible electroporation would otherwise occur, and/or (c) may be concerned about thermal heating and purposely subject a targeted treatment area to a power level that would typically lead to reversible electroporation. One potential benefit of the present disclosure is that irreversible electroporation of these areas may be achieved.

In various embodiments of the present disclosure, the tissue that is subjected to electroporation treatment is heart tissue. For example, as discussed in further below, an ablation catheter may be inserted into the left atrium and energy delivered (a) to the tissue near the ostia of the pulmonary veins in the left atrium (e.g., to treat atrial fibrillation), (b) to the left atrial appendage (e.g., to prevent the heart from dislodging a left atrial appendage closure device such as the Watchman™ from Boston Scientific Corporation, or another cardiac device), or (c) to other heart tissue.

In various embodiments, the calcium ions are delivered in the form of a calcium-ion-containing solution through a balloon catheter that is also used to conduct an electroporation treatment, such that the calcium ions are released in close proximity to the electroporation treatment.

Calcium ions may be delivered, for example, using a solution that contains one or more soluble calcium salts, examples of which include calcium halide salts such as calcium chloride, calcium bromide and calcium iodide, among others; calcium salts of organic acids (including amino acids), such as calcium lactate, calcium citrate, calcium malate, calcium acetate, calcium gluconate, calcium propionate, calcium ascorbate, calcium butyrate, and calcium formate, among others; calcium salts of mixed organic acids such as calcium citrate malate, calcium lactate malate, calcium lactate gluconate, and calcium lactate citrate, among others; and calcium phosphate, among others. Calcium chloride is a particularly beneficial calcium salt as a result of its high solubility and ready availability. However other water soluble calcium salts may be employed as well.

Calcium ion concentrations in the calcium-ion-containing solutions of the present disclosure may be, for example, at least about 250 nM, more typically at least about 1 mM. Calcium ion concentrations in the calcium-ion-containing solutions of the present disclosure may typically range, for example, from 250 nM to 500 mM, more typically ranging from 1 mM to 100 mM. For instance, calcium ion concentrations in the calcium-ion-containing solutions of the present disclosure may range from 250 nM to 500 nM to 1 micromolar (µM) to 10 µM to 100 µM to 250 µM to 500 µM to 1 mM, to 2.5 mM to 5 mM to 10 mM to 25 mM to 50 mM to 100 mM to 250 mM to 500 mM (i.e., calcium ion concentrations may range between any two of the preceding values).

Calcium-ion-containing solutions may be stored, for example, in a syringe, vial, ampoule, bag, or other container (e.g., any container that is configured to interact with an electroporation balloon catheter as described elsewhere herein). One or more soluble calcium salts may also be shipped as a dry composition, for example, in a syringe, vial, ampoule, bag or other container, and may be mixed with a suitable liquid carrier (e.g. sterile water for injection, physiological saline, phosphate buffer, a solution containing an imaging contrast agent, etc.) prior to administration. One or more containers of calcium-ion-containing solution, one or more containers of soluble calcium salts in dry form, and/or one or more containers of liquid carrier may also be supplied to form a kit. Such a kit may also include an electroporation balloon catheter as described elsewhere herein.

Electroporation balloon catheters are described herein wherein an ion-containing solution is released from the surface of the balloon through one or more porous areas on a surface of the balloon ("porous" and "permeable" may be used interchangeably herein to describe balloon catheters regions from which ion-containing solution may be released). In certain embodiments, only a calcium-ion-containing solution is released from the porous areas during treatment. In certain embodiments, an additional ion-containing solution may be released from the porous areas during treatment. For instance, a first ion-containing solution of a salt of a Group 1A metal (e.g., Li, Na, K, etc.) and a halide (e.g., Cl, Br, I, etc.), for example, a sodium chloride solution, or a potassium chloride solution, may be released from the porous areas for purposes of performing the electroporation procedure. Subsequently and/or previously, a second ion-containing solution, more particularly, a calcium-ion-containing solution, may be released from the porous areas for purposes of enhancing cell death.

In certain embodiments, the calcium-ion-containing solution may further comprise a Group 1A metal halide salt (e.g., NaCl, KCl, etc.) to provide enhanced electrical conductivity.

Releasing a calcium-ion-containing solution from the surface of the balloon allows calcium ions to be brought into direct contact with tissue affected by electroporation. In addition, the balloon will help confine the calcium ions to the areas of tissue undergoing electroporation, counteracting dilution of the calcium ions in the treatment area. Consequently, the calcium ions may be delivered before and/or during electroporation in some embodiments. Where calcium ions are delivered prior to electroporation, voltages that are much lower than those used in electroporation may be applied to drive the calcium ions into the cells. The calcium ions may also be delivered after electroporation to ensure minimal dilution of the calcium ions, in which case the voltages may, for example, be the same as that used in electroporation, or may also be of much lower voltages than those used in electroporation, as the voltages at this stage are being used to drive the calcium away from the balloon into the cells. The balloon may also deliver calcium ions to edges of the ablation zone that may have experienced only reversible electroporation, enhancing cell death in those regions. Ultimately, any excess calcium will be diluted in the bloodstream, preventing damage to healthy normal tissue beyond the target tissue.

FIG. 1 shows an exemplary ablation system 100 in accordance with embodiments of the disclosure. As shown, the system 100 includes a catheter 102 sized and shaped for vascular access. The catheter 102 has a distal end 104 and a proximal end 106. In one aspect, the proximal end 106 of the catheter 102 includes a handle 108 having a proximal portion 110 and a distal portion 112. A physician may manipulate the ablation system 100 via the handle 108 during a treatment procedure involving ablation. The handle 108 may include a plurality of conduits, lumens, conductors, and wires to facilitate control of the catheter 102 and/or connection of the catheter 102 with at least one ion-containing solution source 152, for example, a calcium-ion-containing solution, an ablative energy source 154, as well as, in certain embodiments, a mapping source, control software/hardware, a temperature display, and so forth. The handle 108 may further include connection ports 113 through which the at least one ion-containing solution source 152 and the ablative energy source 154, as well as, if desired, a mapping energy source, control software, etc. may be operably coupled.

The catheter 102 can include an elongate body 114 having a proximal end 116 and a distal end 118. The elongate body 114 may house electrical conductors (e.g., wires) for transmitting sensed signals and/or ablation energy. While the elongate body 114 may include a circular cross-sectional geometry, other cross-sectional shapes, such as elliptical, polygonal (e.g., triangular, rectangular, etc.) and various other shapes, can be employed. The elongate body 114 may be made of a variety of materials, including, but not limited to, metals and polymers. In certain instances, the elongate body 114 may be preformed of an inert, resilient material that retains its shape and does not soften significantly at body temperature; for example, Pebax®, polyethylene, or Hytrel®) (polyester). The elongate body 114 may be flexible and capable of winding through a tortuous path that leads to a target tissue region, e.g., an area within the heart. The elongate body 114 may also be semi-rigid, for example, by being made of a stiff material, or by being reinforced with a coating or coil, to limit the amount of flexing.

In certain instances, the movement of the distal end 118 of the elongate body 114 (such as to wind through the tortuous path that leads to a target tissue region) can be controlled by a control mechanism 122 included within the handle 108. The system 100 can include an articulating section of the elongate body 114 (e.g., near the distal end 118) that is controlled via the control mechanism 122. The distal end 118 of the elongate body 114 may be deflected or bent. The articulation section of the body may facilitate insertion of the catheter 102 through a body lumen (e.g., vasculature) and/or placement of electrodes at a target tissue location. The articulation may provide one or more degrees of freedom and permit up/down and/or left/right articulation.

The distal end 104 of the catheter 102 includes a tip section 124 positioned at the distal end 118 of the elongate body 114. The tip section 124 includes a proximal portion 134 and a distal portion 136. In various embodiments instances, the tip section 124 may comprise an electroporation balloon 142.

The electroporation balloon 142 may be configured to conduct radio frequency (RF) energy or direct current (DC) to form lesions during the ablation procedure. For example, the electroporation balloon 142 may deliver ablation energy to the myocardial tissues that are a source of arrhythmia. The electroporation balloon 142 may be coupled to wires 126 using suitable means, such as soldering or welding. The wires 126 can pass through a lumen 144 extending through the elongate body 114 of the catheter 102 and be electrically coupled to a power generator exteriorly coupled to the ablation system 100. The elongate body 114 can also house one or more fluid delivery lumens for introducing ion-containing solution into and removing ion-containing solution from the electroporation balloon 142.

The electroporation balloon 142 may also be configured to measure the localized intracardial electrical activity (map) in real time at the point of energy delivery. The electroporation balloon 142 may allow the physician to ascertain lesion formation by measuring the electrical activity of the tissue having been in contact with an ablation electrode (e.g., the lack of electrical activity indicates ablated tissue, whereas the presence of electrical activity indicates live or non-ablated tissue). In certain instances, the wires 126, coupled to the electroporation balloon 142, may also be electrically coupled to a mapping signal processor such that electrical events in myocardial tissue can be sensed for the generation of electrograms, monophasic action potentials (MAPs), isochronal electrical activity maps, and the like.

Figure 2:
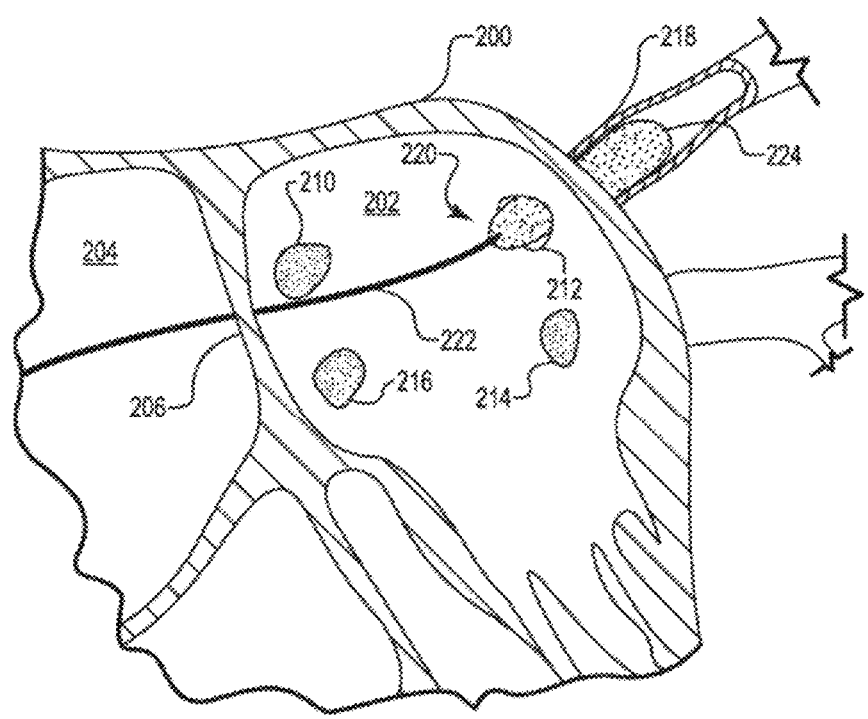
FIG. 2 shows an exemplary ablation system at a target tissue region within patient's heart in accordance with embodiments of the disclosure.

FIG. 2 shows an exemplary ablation system at a target tissue region within patient's heart 200 in accordance with embodiments of the disclosure. More specifically, the heart 200 shown in FIG. 2 may be undergoing a pulmonary vein ablation procedure using a device 220 in accordance with various aspects discussed herein. The device 220 may include a catheter having an elongate body 222 that is connected to a balloon structure 224. The device 220 may be connected to an energy source and controller (e.g., radiofrequency (RF) or direct current (DC) system, not shown) and one or more ion-containing solution sources (not shown), which may be located external to the patient. The balloon structure 224 may be located near the distal end of elongate body 222. One or more interior chambers of the balloon structure 224 may be in fluid communication with one or more fluid delivery lumens arranged within the elongate body 222. The one or more fluid delivery lumens are used to convey the one or more ion-containing solutions from a source external to the patient into the balloon structure 224. The elongate body 222 and the balloon structure 224 may be delivered to a tissue region to which ablation energy may be applied.

As shown in FIG. 2, the elongate body 222 may be positioned in the left atrium 202 of the patient's heart 200. More specifically, in certain instances, the device 220 may enter the right atrium 204 of heart 200 through a femoral vein and the inferior vena cava (not shown). The device 220 may be passed through a puncture in an atrial septum 206 to access left atrium 202. From the left atrium 202, the device 220 may be positioned through any of the pulmonary vein ostia 210, 212, 214, or 216 to enter a pulmonary vein such as pulmonary vein 218. In certain instances, device 220 may be delivered via internal catheter steering, the device 220 may be an over-the-wire device that is delivered over or on a pre-placed guidewire, a delivery catheter/sheath or rapid exchange catheter may be used to assist in the insertion and placement of the device 220, or a combination of the forgoing techniques may be employed.

After positioning of the device 220 at the tissue region (within the pulmonary vein 218 as shown in FIG. 2), the balloon structure 224 may be expanded. The balloon structure 224 may be inflated using an ion-containing solution (e.g., saline, a calcium-ion-containing solution, etc.) as the inflation medium. In instances where the balloon structure 224 is positioned within a vessel such as the pulmonary vein 218, the inflation of balloon structure 224 may cause the outer surface of balloon structure 224 to contact an inner wall of the vessel. In certain instances, contrast agent can be expelled from the catheter (e.g., from the upstream end of the catheter) to ensure that the pulmonary vein 218 is properly sealed. In certain instances, ablation energy may be applied through one or more electrodes (not shown) arranged on or within the balloon structure 224. In addition, one or more portions of the balloon structure 224 may have a permeability such that an ion-containing solution may exude, elute, weep, or otherwise be transmitted from therethrough. In certain instances, the ion-containing solution may be a calcium-ion-containing solution that may contact the inner wall of pulmonary vein 218.

The ablation energy may be applied through one or more portions of the balloon structure 224 by an electric field generated by the external source/controller and transferred through wires within one or more lumens of the elongate body 222 to one or more electrodes (not shown) associated with the balloon structure 224. The electric energy can be transmitted to the inner wall of pulmonary vein 218 directly from one or more electrodes on the surface of balloon structure 224 and/or from one or more electrodes within the balloon structure 224 via the ion-containing solution that exudes from the exterior surface of balloon structure 224. The electric field may modulate the activity along neural fibers within the wall of the pulmonary vein 218 by at least partially causing cell death to the tissue receiving the ablation energy. In certain instances, while the electric field for ablation is being applied, transmission of the ion-containing solution from the balloon structure 224 to the tissue can be continued.

The ablation process may be performed concurrently with the delivery of a calcium-ion-containing solution to the tissue receiving the ablation energy, or the ablation process may be performed sequentially with the delivery of the calcium-ion-containing solution. For example, a first ion-containing solution of a halide salt of a Group 1A metal, for instance, a sodium chloride solution, may be released from the balloon structure 224 for purposes of performing the electroporation procedure. Subsequently and/or previously, a calcium-ion-containing solution may be released from the balloon structure 224 for purposes of enhancing cell death.

In certain instances, the electric field may be generated by applying direct current to the one or more electrodes arranged within the balloon structure 224. The use of direct current may cause cell death to the tissue receiving the ablation energy. The direct current may form pores in the cells of the wall of the pulmonary vein 218 that are reversible or irreversible (e.g., the pores do not close). The balloon structure 224 being in contact with the wall of the pulmonary vein 218 may provide controlled and direct ablation of a target area while mitigating against down-stream proliferation of the ablation energy.

Balloon structures 224 for use in accordance with the present disclosure may be formed from a variety of materials including the following, including combinations thereof, among others: polyurethanes, including thermoplastic polyurethanes, for example, polycarbonate-based polyurethanes (e.g. BIONATE, CHRONOFLEX, etc.), polyether-based polyurethanes, polyester-based polyurethanes, polyether- and polyester-based polyurethanes (e.g. TECOTHANE, PELLETHANE, etc.), polyisobutylene-based polyurethanes, and polysiloxane-based polyurethanes, among others; styrene-alkylene block copolymers, including styrene-isobutylene block copolymers such as poly(styrene-b-isobutylene-b-styrene) (SIBS) tri-block copolymers and styrene-isoprene-butadiene block copolymers, among others; fluoropolymers, including polyvinylidene fluoride (PVDF), poly(vinylidene fluoride-co-hexafluoropropene) (PVDF-HFP), and polytetrafluoroethylene (PTFE), among others; polyesters, including non-biodegradable polyesters such as polyethylene terephthalate and biodegradable polyesters such as polycaprolactone (PCL) and poly(lactic-co-glycolic acid) (PLGA), among others; silicones including polydimethylsiloxane, among others; and polyamides, including nylon (e.g., nylon 6) and polyether block amides, among others.

Balloons having porous and nonporous regions may be provided by any method known in the art. In certain beneficial embodiments, such balloons may be formed in conjunction with a fiber-forming process such as electrospinning, force spinning or melt-blowing, among other possible processes. Electrospinning is a process that uses electrical charge to create polymer fibers from a polymer-containing fluid (e.g., a polymer solution or polymer melt). Force spinning is a process that uses centrifugal force to create fibers. Melt-blowing is a process in which a polymer melt is extruded through a die and then stretched and cooled with high-velocity air to form fibers.

Solvents for forming polymer solutions for spinning processes such as electrospinning or force spinning will depend on the polymer that is in solution and include, for example, acetone, acetonitrile, heptane, dimethyl-formamide (DMF), dimethylacetamide (DMAC), ethanol, ethyl acetate, methanol, 1-propanol, 2-propanol, tetrahydrofuran (THF), toluene, xylene, and combinations thereof, among others. Typical voltages for electrospinning range between 5000-30000 volts, among other possibilities.

In certain embodiments, polymer fibers may be formed into an interior cavity of a balloon-shaped mold or onto an exterior surface of a balloon-shaped mold using a suitable fiber forming process (e.g., an electrospinning process, etc.), or preformed polymer fibers may be placed into an interior cavity of a balloon-shaped mold or onto an exterior surface of a balloon-shaped mold. The mold may be formed from a removable material, for example, a material that may subsequently be melted or dissolved. In certain embodiments, polymer fibers are formed onto an external surface of a balloon-shaped mold that is formed of ice.

Once fibers are assembled in the shape of a balloon (e.g., while still remaining in or on a mold, or after removal from a mold), a curable fluid material such as a fluid room temperature curable material, a fluid thermoset material or a fluid UV curable material, e.g. a curable polydimethylsiloxane (PDMS) material, among many others, or a thermoplastic melt, may be applied to the fibers in those areas where it is desired to establish one or more nonporous regions. Upon curing (in the case where a curable material is employed) or cooling (in the case where a thermoplastic melt is employed), a balloon having porous and nonporous regions is produced.

In one particular example, a UV curable adhesive such as Med-1515 RTV silicone room temperature adhesive, available from NuSil™ Technology LLC, Carpinteria, CA, may be applied to the fibers to plug up small gaps in the fibrous structure, thereby creating one or more non-porous regions. The adhesive may be non-diluted or diluted with heptane or xylene. Adhesive:solvent mass/mass dilution levels may range, for example, from 3:1 to 1:5 (e.g., 3:1, 2:1, 1:1, 1:2, 1:3, 1:4 or 1:5), among other values.

In an alternative process, a curable fluid material or a thermoplastic melt may be applied to an interior cavity of a balloon-shaped hollow mold or onto an exterior surface of a balloon-shaped internal mold in those areas where nonporous regions are desired. While the material remains at least partially in fluid form (e.g., where the thermoset material is uncured or only partially cured or where the thermoplastic material is held at or above its melting point), polymer fibers may be applied onto the material, for example, using an electrospinning process or an alternative process. Because the material is at least partially in fluid form, at least a portion of the polymer fibers penetrates into the material. Upon curing (in the case where a curable material is employed) or cooling (in the case where a thermoplastic melt is employed), a balloon having porous and nonporous regions is produced.

Using the above and other methods, a balloon structure having a proximal end, a distal end, a porous region, a nonporous region and at least one interior chamber is formed.

During irreversible electroporation (IRE), one or more porous areas of the electrospun balloon are placed in the vicinity of tissue that is being treated. Unlike radiofrequency energy or thermal injury from DC ablation, IRE does not require contact with tissue. Rather, it works by having an overlying electrical field cause electroporation of a cell membrane, and subsequent cell death. Applied voltages employed for irreversible electroporation may vary from application to application, and for the systems described herein, typical applied voltages may range, for example, from 1000 V to 3000 V, among other possibilities. Electric field strengths may range, for example, from 400 V/cm to 3000 V/cm, among other possibilities. Pulse times employed for irreversible electroporation may also vary from application to application, and for the systems described herein, voltages are typically applied as pulses ranging from 0.5 μs to 200 μs, more typically from 10 μs to 100 μs, among other possibilities. Between 10 and 200 pulses may be delivered, among other possibilities.

As previously indicated, in some embodiments, lower voltages that those used in electroporation may be used in conjunction with calcium delivery. In these embodiments, applied voltages may range, for example, from 200 V to 400 V, among other possibilities and electric field strengths may range, for example, from 80 V/cm to 400 V/cm, among other possibilities.

Figure 3:
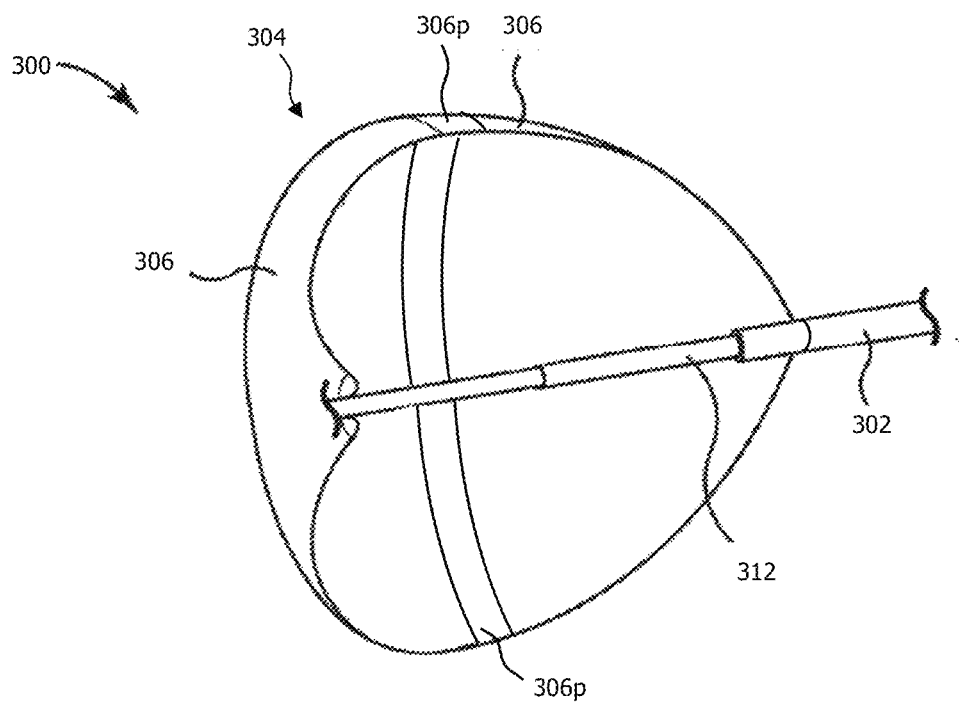
FIG. 3 is a schematic cutaway view of a distal end of a catheter that comprises a single-chamber porous balloon structure, in accordance with embodiments of the present disclosure.

In certain embodiments, the procedures described herein may be provided in conjunction with devices in which electrical energy is delivered, for example, an irreversible electroporation (IRE) balloon device, in which one or more electrodes are positioned FIG. 3 shows a cutaway illustration of an exemplary apparatus 300 for applying ablation therapy to a tissue region in accordance with embodiments of the disclosure. The apparatus 300 includes a catheter having an elongate body 302. At or near a distal portion of the elongate body 302 is a balloon structure 304. The balloon structure 304 may be attached to or formed on the elongate body 302.

The balloon structure 304 may include a first portion 306, at least a section of which has a first permeability. The balloon structure 304 is configured to inflate in response to a fluid inflation medium, such as an ion-containing solution, being provided thereto. Moreover, the first portion 306 of the balloon structure 304 may be configured to permeate the fluid therethrough in response to inflation of the balloon structure 304 (the fluid may be, for example, an ion-containing solution such as saline or a calcium-ion-containing solution) while at the same time anchoring the elongate body 302 at a tissue region.

For example, the balloon structure 304 may include a porous region 306$p$ in the first portion 306 that is permeable to fluid, while a remainder of the first portion 306 is substantially impermeable to fluid. Thus, at least a portion 306$p$ of the balloon structure 304 may be permeable.

The balloon structure 304 may be positioned at a target tissue region for ablation. The balloon structure 304 may be configured to deploy within a body lumen such as a vessel or heart chamber such that the porous region 306$p$ is adjacent the wall of the body lumen. The first portion 306 may permeate the fluid (e.g., ion-containing solution) to the tissue region (e.g., the wall of the body lumen) through porous region 306$p$.

The apparatus 300 may also include one or more electrodes configured to deliver energy to a tissue region. As shown in FIG. 3, the apparatus 300 includes an electrode 312 arranged within the balloon structure 304. In certain instances, the electrode 312 may be arranged within the first portion 306 and configured to deliver energy in response to a direct current applied thereto. The energy from the electrode 312 may be applied through an external surface of the first portion 306 of the balloon structure 304 by an electric field generated by an external source/controller (not shown) and transferred through a wire within the elongate body 302. The electric energy can be transmitted to the tissue region (e.g., the vessel wall) via the ion-containing solution that exudes from through porous region 306p of the first portion 306 of the balloon structure 304. The electric field may at least partially cause cell death to the tissue receiving the energy. In certain instances, while an electric field for ablation is being applied, transmission of the ion-containing solution through porous region 306p of the first portion 306 of the balloon structure 304 to the tissue can be continued. In this regard, an electric field may be applied while continuously pumping ion-containing solution into the balloon or may be applied while flow of ion-containing solution into the balloon is ceased for a short time period, during which the ion-containing solution continues to leak from the balloon due to the residual pressure in the balloon.

In certain instances, as noted above, the electric field may be generated by applying direct current to the electrode 312. The use of direct current may cause cell death to the tissue receiving the ablation energy. The direct current may form pores in the cells of the tissue region that are reversible or irreversible (e.g., the pores do not close). The balloon structure 304 being adjacent the tissue may provide controlled and direct ablation of a target area while mitigating against down-stream proliferation of the ablation energy. Moreover, by delivering calcium ions in accordance with the present disclosure, areas of irreversible electroporation may be created in areas where reversible electroporation would otherwise occur in the absence of the calcium ions, thereby increasing the effectiveness of the irreversible electroporation treatment.

In certain embodiments, the ion-containing solution that is released from the balloon structure 304 during application of electrical energy is a calcium-ion-containing solution.

In certain embodiments, a first ion-containing solution is released from the balloon structure 304 during application of electrical energy that is not calcium-ion-containing solution (e.g., the first ion-containing solution may be a Group 1A halide solution, such as sodium chloride), and a calcium-ion-containing solution is released before and/or after the application of electrical energy. In one particular example, a calcium-ion-containing solution is introduced into the balloon structure 304 after the application of electrical energy. For instance, a calcium-ion-containing solution may be introduced into the balloon structure 304 via a first fluid delivery lumen and while at the same time removing fluid from the balloon structure 304 via a second fluid delivery lumen. Because the introduction of calcium-ion-containing solution into the balloon structure 304 containing the first ion-containing solution will result in a mixture of the calcium-ion-containing solution and the first ion-containing solution, the concentration of the calcium ions in the calcium-ion-containing solution that is introduced into the balloon structure 304 will be greater than the concentration of calcium ions that is ultimately released from the porous region 306p or the balloon structure 304.

Figure 4:
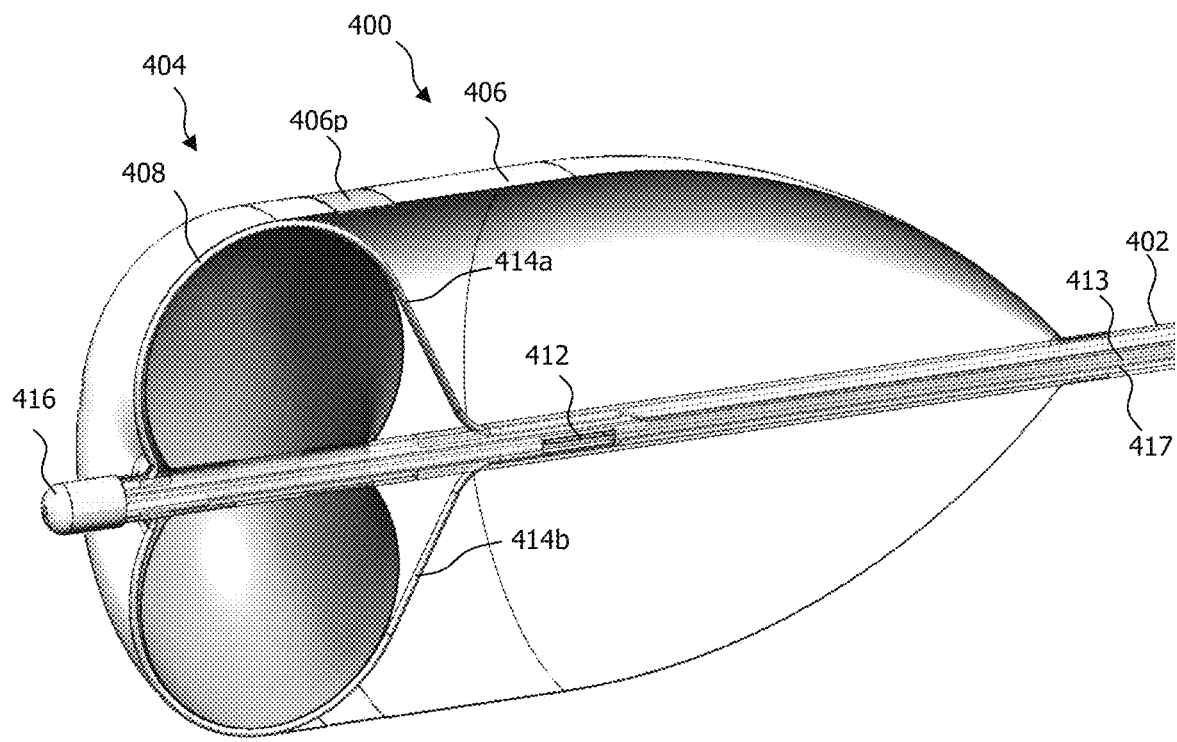
FIG. 4 is a schematic cutaway view of a distal end of a catheter that comprises a dual-chamber porous balloon structure, in accordance with embodiments of the present disclosure.

Another embodiment is illustrated in FIG. 4, which shows a cutaway illustration of another exemplary apparatus 400 for applying ablation therapy to a tissue region in accordance with the disclosure. The apparatus 400 includes a catheter having an elongate body 402. At or near a distal portion of the elongate body 402 is a balloon structure 404. The balloon structure 404 may be attached to or formed on the elongate body 402.

The balloon structure 404 may include a first portion 406 of that forms a first chamber and a second portion 408 that forms a second chamber. The first portion 406 may be deposited or attached onto the second portion 408. The balloon structure 404 may include a porous region 406p in the first portion 406 that is permeable to ion-containing solution, while a remainder of the first portion 406 may be substantially impermeable to ion-containing solution. The second portion 408 may be substantially impermeable to ion-containing solution. The balloon structure 404 may be configured to inflate in response to an inflation medium, for example, an ion-containing solution, being provided thereto. In certain instances, the first portion 406 and the second portion 408 may be inflated using a single inflation medium, or the first portion 406 and the second portion 408 may be separately inflated using a first inflation medium and a second inflation medium. As a result, in certain instances, the first portion 406 of the balloon structure 404 may be configured to permeate an ion-containing solution therethrough in response to inflation of the balloon structure 404 (the ion-containing solution may be, for example, saline or a calcium-ion-containing solution, etc.) and the second portion 408 of the balloon structure 404 may be configured to anchor the elongate body 402 at a tissue region.

The balloon structure 404 may be positioned at a target tissue region for ablation. For example, the balloon structure 404 may be configured to deploy within a body lumen (e.g., a blood vessel, atrium, etc.) such that the porous region 406p is adjacent the wall of the body lumen. The porous region 406p may permeate the ion-containing solution to the tissue region (e.g., the wall body lumen wall). In addition, the second portion 408 may be configured to anchor the elongate body 402 at the tissue region.

The apparatus 400 may include one or more electrodes configured to deliver energy to a tissue region. As shown in FIG. 4, the apparatus includes an electrode 412 arranged within the balloon structure 404. In certain instances, the electrode 412 may be arranged within the first portion 406 and configured to deliver energy in response to a direct current applied thereto. The energy from the electrode 412 may be applied through an external surface of the first portion 406 of the balloon structure 404 by an electric field generated by an external source/controller (not shown) and transferred through a wire 413 within the elongate body 402. The electrical energy can be transmitted to the tissue region (e.g., the vessel wall) via the ion-containing solution that exudes from the porous region 406p of the first portion 406. The electric field may at least partially cause cell death to the tissue receiving the energy. In certain instances, while an electric field for ablation is being applied, transmission of the ion-containing solution from the porous region 406p of the first portion 406 of the balloon structure 404 to the tissue can be continued.

In certain instances, and as noted above, the electric field may be generated by applying direct current to the electrode 412. The use of direct current may cause cell death to the tissue receiving the ablation energy. The direct current may form pores in the cells of the tissue region that are reversible or irreversible (e.g., the pores do not close). The balloon structure 404 being adjacent the tissue may provide controlled and direct ablation of a target area while mitigating against down-stream proliferation of the ablation energy. Moreover, by delivering calcium ions in accordance with the present disclosure, areas of irreversible electroporation may be created in areas where reversible electroporation would otherwise occur in the absence of the calcium ions, thereby increasing the effectiveness of the irreversible electroporation treatment.

The apparatus 400 may also include a tip electrode 416 that is configured to form a ground or a closed-loop with the electrode 412. Like the electrode 412, the tip electrode 416 may be coupled to the external source/controller via a wire 417 within the elongate body 402. The external source/controller may apply, for example, RF ablation energy or DC current.

In certain instances, the electrode 412 and/or the tip electrode 416 may also be configured to measure the localized intracardial electrical activity. The wire 413 and/or the wire 417 may also be electrically coupled to a mapping signal processor such that electrical events in myocardial tissue can be sensed for the generation of electrograms, monophasic action potentials (MAPs), isochronal electrical activity maps, and the like. The electrode 412 and/or the tip electrode 416 may allow the physician to measure the electrical activity of the tissue region (e.g., the lack of electrical activity indicates ablated tissue, whereas the presence of electrical activity indicates live tissue).

In some instances, the apparatus 400 may also include pacing electrodes 414a, 414b. The pacing electrodes 414a, 414b may be arranged within the balloon structure 404. The pacing electrodes 414a, 414b may be electrically coupled to a mapping signal processor such that electrical events in myocardial tissue can be sensed for the generation of electrograms, monophasic action potentials (MAPs), isochronal electrical activity maps, and the like. The pacing electrodes 414a, 414b may allow the physician to measure the electrical activity of the tissue region (e.g., the lack of electrical activity indicates ablated tissue, whereas the presence of electrical activity indicates live tissue). The ablation energy applied via the electrode 412 may be altered based on the electrical activity measured by the pacing electrodes 414a, 414b, which may be used to determine a target location for the ablation therapy.

Figure 5:
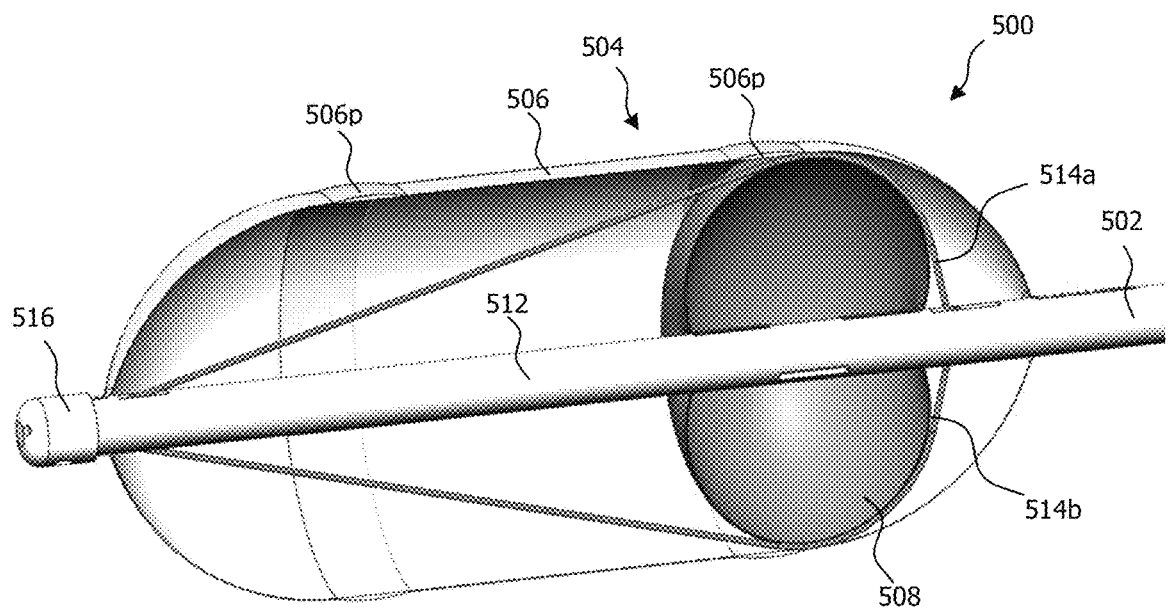
FIG. 5 is a schematic cutaway view of a distal end of a catheter that comprises a dual-chamber porous balloon structure, in accordance with embodiments of the present disclosure.

Another embodiment is illustrated in FIG. 5, which shows a cutaway illustration of an exemplary apparatus 500 for applying ablation therapy to a tissue region in accordance with embodiments of the disclosure. The apparatus 500 includes a catheter having an elongate body 502. At or near a distal portion of the elongate body 502 is a balloon structure 504.

Analogous to FIG. 4, balloon structure 504 of FIG. 5 may include a first portion 506 of that forms a first chamber and a second portion 508 that forms a second chamber. The balloon structure 504 may include two porous regions 506p in the first portion 506 that are permeable to ion-containing solution, while a remainder of the first portion 506 is substantially impermeable to ion-containing solution. The second portion 508 may be substantially impermeable to ion-containing solution. The balloon structure 504 may be configured to inflate in response to an inflation medium being provided thereto. In certain instances, the first portion 506 and the second portion 508 may be inflated using a single inflation medium (e.g., ion-containing solution), or the first portion 506 and the second portion 508 may be separately inflated using a first inflation medium and a second inflation medium. As a result, in certain instances, the first portion 506 of the balloon structure 504 may be configured to permeate an ion-containing solution therethrough in response to inflation of the balloon structure 504 (the ion-containing solution may be, for example, saline, a calcium-ion-containing solution, etc.) and the second portion 508 of the balloon structure 504 may be configured to anchor the elongate body 502 at a tissue region.

The balloon structure 504 may be positioned at a target tissue region for ablation. The balloon structure 504 may be configured to deploy within a body lumen (e.g., a blood vessel, atrium, etc.) such that porous regions 506p are adjacent the wall of the body lumen. The porous regions 506p may permeate the ion-containing solution to the tissue region (e.g., the wall of the body lumen). In addition, the second portion 508 may be configured to anchor the elongate body 502 at the tissue region.

Analogous to FIG. 4, the apparatus 500 of FIG. 5 may include an electrode 512 arranged within the balloon structure 504, a tip electrode 516 that is configured to form a ground or a closed-loop with the electrode 512, and pacing electrodes 514a, 514b. These components may be operated in a fashion analogous to that described in conjunction with FIG. 4.

Figure 6:
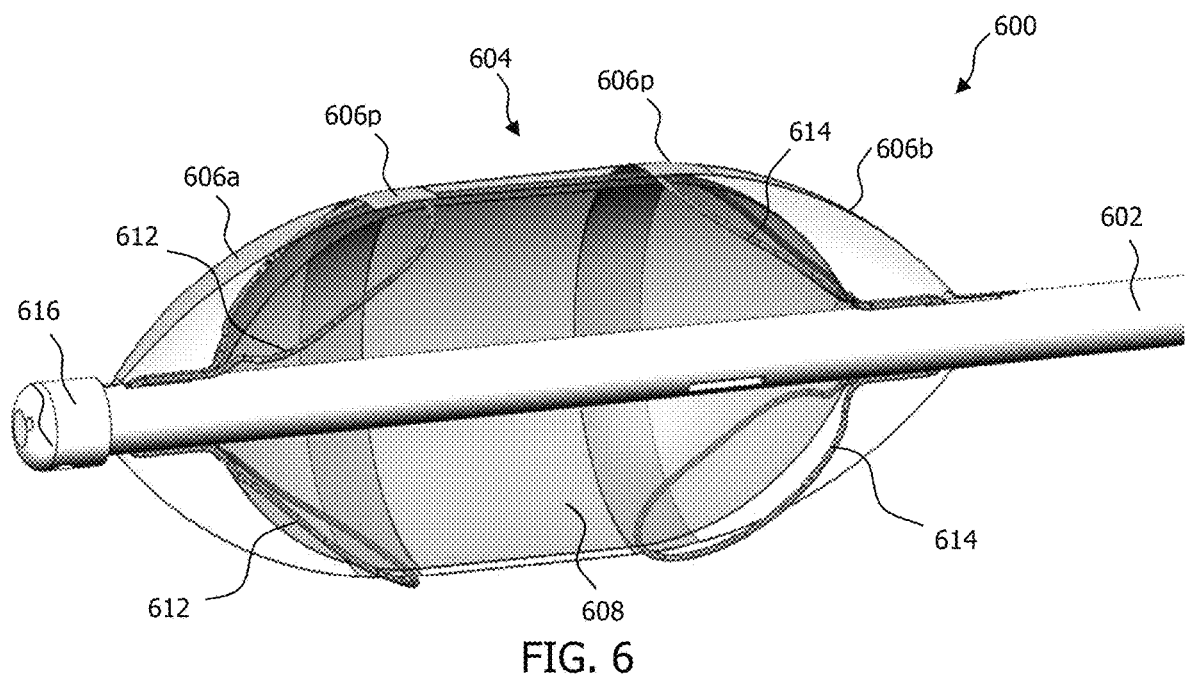
FIG. 6 is a schematic cutaway view of a distal end of a catheter that comprises a three-chamber porous balloon structure having radiopaque markers, in accordance with an embodiment of the present disclosure.

Still another embodiment is illustrated in FIG. 6, which shows a cutaway illustration of an exemplary apparatus 600 for applying ablation therapy to a tissue region in accordance with the present disclosure. The apparatus 600 includes a catheter having an elongate body 602. At or near a distal portion of the elongate body 602 is a balloon structure 604.

The balloon structure 604 of FIG. 6 may include a first portion 606a of that forms a first chamber, a second portion 608 that forms a second chamber, and a third portion 606b that forms a third chamber. The balloon structure 604 may include two porous regions 606p, one in the first portion 606a and another in the third portion 606b, which are permeable to ion-containing solution, while a remainder of the first and third portions 606a, 606b are substantially impermeable to ion-containing solution. The second portion 608 may be substantially impermeable to ion-containing solution. The balloon structure 604 may be configured to inflate in response to an inflation medium being provided thereto. In certain instances, the first portion 606a, the second portion 608, and the third portion 606b, may be inflated using a single inflation medium (e.g., ion-containing solution), or the first portion 606a, the second portion 608, and the third portion 606b may be separately inflated using separate inflation media. As a result, in certain instances, the first and third portions 606a, 606b of the balloon structure 604 may be configured to permeate an ion-containing solution therethrough in response to inflation of the balloon structure 604 (the ion-containing solution may be, for example, saline, a calcium-ion-containing solution, etc.) and the second portion 608 of the balloon structure 604 may be configured to anchor the elongate body 602 at a tissue region.

The balloon structure 604 may be positioned at a target tissue region for ablation. The balloon structure 604 may be configured to deploy within a body lumen (e.g., a blood vessel, atrium, etc.) such that one or both of the porous regions 606p are adjacent the wall of the body lumen. The porous regions 606p may permeate the ion-containing solution to the tissue region (e.g., the vessel wall). In addition, the second portion 608 may be configured to anchor the elongate body 602 at the tissue region.

The balloon structure 604 of FIG. 6 also includes electrodes 612 in the first portion 606a, electrodes 614 in the third portion 606b, and a tip electrode 616. The electrode 612 may be configured to form a ground or a closed-loop with the electrode 614. Each of the electrodes 612, 614 may also be configured to form a ground or a closed-loop with the tip electrode 616. These components may be operated in a fashion analogous to that described in conjunction with FIG. 4.

Figure 7:
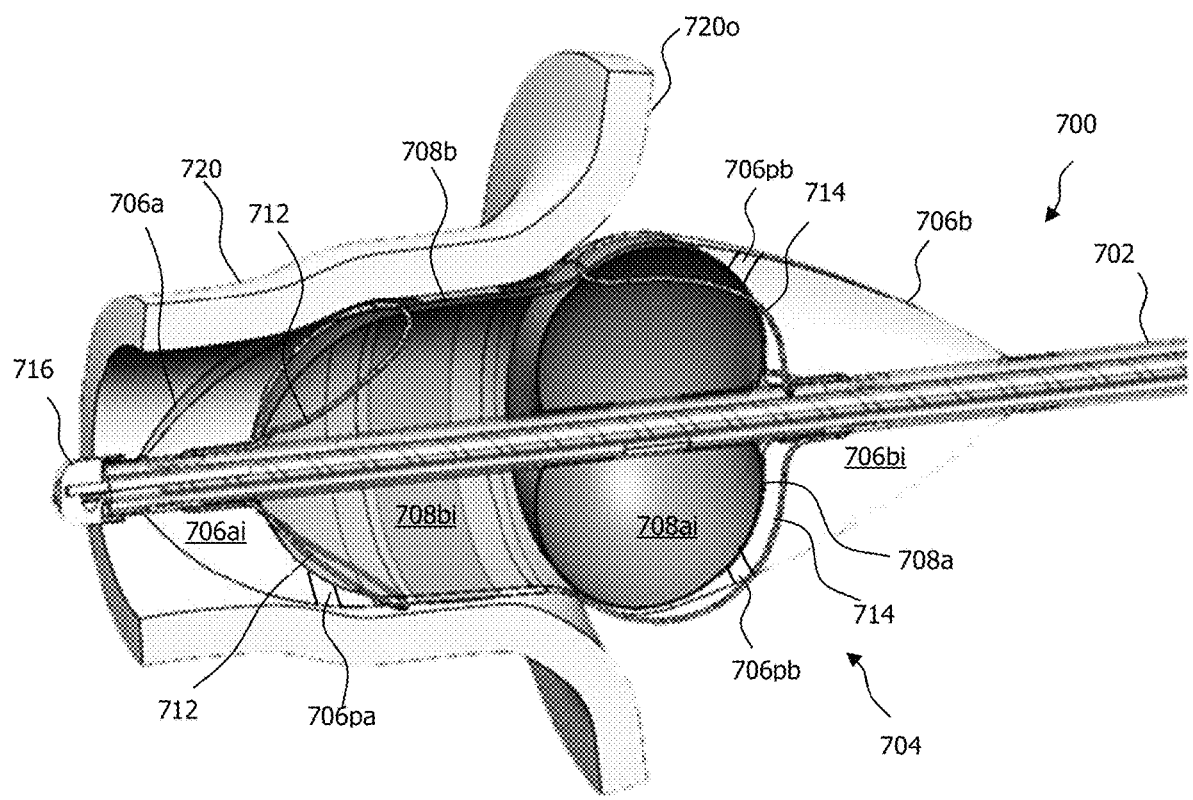
FIG. 7 is a schematic cutaway view of a distal end of a catheter that comprises a porous balloon structure positioned in a vein near an ostium of the vein, in accordance with embodiments of the present disclosure.

Still another embodiment is illustrated in FIG. 7, which shows a cutaway illustration of an exemplary apparatus 700 for applying ablation therapy to a tissue region in accordance with the present disclosure. The apparatus 700 includes a catheter having an elongate body 702. At or near a distal portion of the elongate body 702 is a balloon structure 704.

The balloon structure 704 of FIG. 7 may include a first portion 706a of that forms a first chamber 706ai, second portions 708a, 708b that form second chambers 708ai, 708bi and a third portion 706b that forms a third chamber 706bi. Although there are two second portions 708a, 708b that form two second chambers 708ai, 708bi in the embodiment shown in FIG. 7, in other embodiments (e.g., analogous to FIG. 6), a single second portion with single second chamber may be employed.

The balloon structure 704 may further include two porous regions 706pa, 706pb, one in the first portion 706a and another in the third portion 706b, which are permeable to ion-containing solution, while a remainder of the first and third portions 706a, 706b are substantially impermeable to ion-containing solution. The second portions 708a, 708b may be substantially impermeable to ion-containing solution. The balloon structure 704 may be configured to inflate in response to an inflation medium being provided thereto. In certain instances, the first portion 706a, the second portions 708a, 708b, and the third portion 706b, may be inflated using a single inflation medium (e.g., ion-containing solution), or the first portion 706a, the second portions 708a, 708b, and the third portion 706b may be separately inflated using separate inflation media. As a result, in certain instances, the first and third portions 706a, 706b of the balloon structure 704 may be configured to permeate an ion-containing solution therethrough in response to inflation of the balloon structure 704 (the ion-containing solution may be, for example, saline, a calcium-ion-containing solution, etc.) and the second portions 708a, 708b of the balloon structure 704 may be configured to anchor the elongate body 702 at a tissue region The balloon structure 704 may be positioned at a target tissue region for ablation. The balloon structure 704 may be configured to deploy within a body lumen (e.g., a blood vessel, atrium, etc.) such that at least one of the porous regions 706pa, 706pb is adjacent the body lumen wall. In this way, at least one of the porous regions 706pa, 706pb may permeate the ion-containing solution to the tissue region (e.g., the wall of the body lumen). In addition, the second portions 708a, 708b may be configured to anchor the elongate body 702 at the tissue region. For example, as seen in FIG. 7, the balloon structure 704 may be expanded in a vein 720 near an ostium 720o of the vein 720 such that the porous region 706pa is adjacent to the wall of the vein 720.

The balloon structure 704 of FIG. 7 may also include electrodes 712 in the first portion 706a, electrodes 714 in the third portion 706b, and a tip electrode 716. The electrodes 712 may be configured to form a ground or a closed-loop with the electrodes 714 and/or form a ground or a closed-loop with the tip electrode 716. These components may be operated in a fashion analogous to that described in conjunction with FIG. 4.

For example, in certain instances, an electric field may be generated by applying direct current to the electrode 712. As previously indicated, the use of direct current may cause cell death to the tissue receiving the ablation energy. The balloon structure 704 being adjacent the tissue may provide controlled and direct ablation of a target area while mitigating against down-stream proliferation of the ablation energy. Moreover, by delivering calcium ions in accordance with the present disclosure, areas of irreversible electroporation may be created in areas where reversible electroporation would otherwise occur in the absence of the calcium ions, thereby increasing the effectiveness of the irreversible electroporation treatment.

In certain embodiments, the ion-containing solution that is released from the porous regions 706pa, 706pb during application of electrical energy may be a calcium-ion-containing solution.

In certain embodiments, a first ion-containing solution is released from the porous region 706pa, 707pb during application of electrical energy that is not calcium-ion-containing solution (e.g., the first ion-containing solution may be a Group 1A halide solution, such as sodium chloride), and a calcium-ion-containing solution may be released from at least one of the porous regions 706pa, 706pb before and/or after the application of electrical energy. In one particular example, for the embodiment shown, a first ion-containing solution (e.g., saline solution) is introduced into the first chamber 706ai of the first portion 706a during the application of electrical energy, and a calcium-ion-containing solution is introduced into the first chamber 706ai of the first portion 706a after the application of electrical energy. For instance, a calcium-ion-containing solution may be introduced into the first chamber 706ai of the first portion 706a via a first fluid delivery lumen (not shown) and while at the same time removing fluid from the first portion 706a via a second fluid delivery lumen (not shown). Because the introduction of calcium-ion-containing solution into the first chamber 706ai of first portion 706a containing the first ion-containing solution will result in a mixture of the calcium-ion-containing solution and the first ion-containing solution, the concentration of the calcium ions in the calcium-ion-containing solution that is introduced from the first fluid delivery lumen into the first chamber 706ai of the first portion 706a will be greater than the concentration of calcium ions that is ultimately released from the porous region 706pa.

What is claimed is:

1. A method for applying ablation therapy to a target tissue region within a patient's heart, the method comprising:
   navigating a catheter to the target tissue region within the patient's heart, the catheter including an elongate body having a proximal portion and a distal portion and a balloon structure positioned at the distal portion of the elongate body, the balloon structure comprising a porous region that is permeable to a calcium-ion-containing solution that comprises one or more calcium salts, and a nonporous region;
   anchoring the nonporous region of the balloon structure at the target tissue region of the patient's heart;
   positioning the porous region of the balloon structure adjacent the target tissue region;
   delivering energy to the target tissue region of the patient's heart; and
   eluting the calcium-ion-containing solution from the balloon structure before, during, and/or after delivering the energy to the target tissue region of the patient's heart to create areas of irreversible electroporation.

2. The method of claim 1, comprising eluting the calcium-ion-containing solution during delivery of the energy to the target tissue region.

3. The method of claim 1, comprising eluting the calcium-ion-containing solution after delivery of the energy to the target tissue region.

4. The method of claim 1, comprising eluting a solution containing a Group IA metal halide salt from the balloon structure before and/or during delivery of the energy to the target tissue region, and eluting the calcium-ion-containing solution after delivery of the energy to the target tissue region.

5. The method of claim 1, wherein eluting a calcium-ion containing solution comprises eluting a concentration of calcium ions in the calcium-ion-containing solution of at least 250 nM.

6. The method of claim 1, wherein eluting a calcium-ion containing solution comprises eluting a concentration of calcium ions in the calcium-ion-containing solution ranging from 250 nM to 500 mM.

7. The method of claim 1, wherein eluting a calcium-ion containing solution comprises eluting a calcium-ion-containing solution comprising one or more calcium salts selected from the group consisting of: calcium halide salts, calcium salts of organic acids, calcium phosphate, calcium chloride, and combinations thereof.

* * * * *